(12) United States Patent
Maeda et al.

(10) Patent No.: US 6,716,426 B1
(45) Date of Patent: Apr. 6, 2004

(54) ANTITUMOR AGENTS

(75) Inventors: Hiroshi Maeda, 3-21-24, Koto, Kumamoto-shi, Kumamoto (JP); Tomohiro Sawa, Kumamoto (JP); Takaaki Akaike, Kumamoto (JP)

(73) Assignee: Hiroshi Maeda, Kumamoto-ken (JP)

( * ) Notice: Subject to any disclaimer, the term of this patent is extended or adjusted under 35 U.S.C. 154(b) by 0 days.

(21) Appl. No.: 09/536,017

(22) Filed: Mar. 27, 2000

Related U.S. Application Data (62) Division of application No. 09/136,522, filed on Aug. 19, 1998, now abandoned.

(30) Foreign Application Priority Data

Aug. 22, 1997 (JP) .............................................. 9-240235

(51) Int. Cl.⁷ .......................... A61K 38/43; A61K 38/44; A61K 38/00
(52) U.S. Cl. .......................... 424/94.1; 424/94.4; 514/2
(58) Field of Search ............................. 514/2; 424/94.1, 424/94.4

(56) References Cited

PUBLICATIONS

Springer et al (European J. Cancer, 1991, 27:13161–1366).*
Matsumura et al (Cancer Res., 1986, 46:6387–6392).*
Eno–Amooquaye et al (CBritish J. Can., 1996, 73:1323–1327).*
Chen et al (Biochimica et Biophysica Acta, 660:293–298).
Yoshikawa et al (Cancer Res., 5:1617–1620.

* cited by examiner

*Primary Examiner*—Susan Ungar
(74) *Attorney, Agent, or Firm*—Nixon & Vanderhye P.C.

(57) ABSTRACT

An antitumor agent, which is a combination of an oxidoreductase, such as xanthine oxidase chemically conjugated to a polymer such as poly ethylene glycol, for initial administration and accumulation in the tumor tissue followed by administration of a substrate for the oxidoreductase which releases reactive oxygen species. Improved tumor selective cytotoxic activity results.

1 Claim, 6 Drawing Sheets

ANTITUMOR AGENTS

This application is a division of application Ser. No. 09/136,522 filed Aug. 19, 1998, now abandoned.

BACKGROUND OF THE INVENTION (a) Field of the Invention

The present invention relates to a group of antitumor agents which by themselves are not toxic and exhibit an improved tumor selective cytotoxic action due to their preferential accumulation in tumor tissue only after subsequent administration of nontoxic substrate components, and a method for treating cancer by administration of these antitumor agents.

More specifically, it relates to the use of non-toxic antitumor agents consisting oxidoreductases, such as xanthine oxidase, which are chemically conjugated with polymers, and time lapse injection of the enzyme's substrates, such as hypoxanthine or xanthine.

(b) Description of the Prior Art

Several antitumor agents such as mitomycin and doxorubicin have been found to exhibit their antitumor effect based on their capability of generating reactive oxygen molecular species. An earlier work by R. Bray and his co-workers (Nature, vol.182, p.1144–1146, 1958) and more recently T. Yoshikawa and his co-workers (Cancer Res., vol.55: p.1617–1620, 1995) reported that the antitumor activity of xanthine oxidase (hereinafter referred to as "XO") is achieved probably via the generation of reactive oxygen molecular species. However, a more critical reevaluation of the antitumor effect of native XO by R. Bray and J. C. Swann showed that the effect was insignificant (Structure and Bonding, vol.11, p.107–144, 1972, published by Elsevior, a note added in footnote of page 112). This was also confirmed again by the sent inventors.

Reactive oxygen molecular species generated from those antitumor drugs exhibit an antitumor effect based on their highly cytotoxic nature. However systemic distribution of those drugs causes undesirable side effects (J. Clin. Invest., vol.98, p.1253–1260, 1996). For instance, native XO readily binds to blood vessels after the administration into blood due to its high binding affinity to vascular endothelial cells (Biochem. J., vol.289, 523–527, 1993). The binding of XO to blood vessels is expected to cause serious side effects such as: i) The superoxide anion radical generated from XO would oxidatively damage blood vessels; ii) The reaction between the superoxide and endogenously formed nitric oxide leads to dilatation of the blood vessels and lowers the blood pressure or thus regulates the blood pressure (Pharmacol. Rev., vol.43, p.109–142, 1991), which would cause hypertension due to lowered level of nitric oxide in the blood vessels (Proc. Natl. Acad. Sci. USA, vol.88, p.10045–10048, 1991), iii) The reaction product of superoxide and nitric oxide, namely the peroxynitrite ($ONOO^-$) further oxidatively damages the blood vessels. Therefore it is not advisable to employ native XO for clinical use. In addition, endogenous anti-XO antibody (Brit. J. Biomed. Sci., vol.51,124–127, 1994) may reduce the activity of XO after intravenous injection.

To enhance the drug efficacy while reducing the systemic side effects, it is necessary to deliver this antitumor enzyme selectively to the tumor tissue. The inventors previously found that macromolecular drugs and lipids preferentially accumulate in the tumor tissue compared with other normal organs, and furthermore they are retained in the tumor tissue for a longer period. This phenomenon is called the EPR effect (enhanced permeability and retention effect), Cancer Res., vol.46,p.638–792, (1986). The enhanced therapeutic efficacy and the reduction of side effects could be achieved by increasing the molecular weight of the antitumor agent (J. Controlled Rel., vol 19, p.315–324, 1992).

The object of the present invention is to provide a group of antitumor agents which exhibit an improved tumor selective accumulation and therefore an improved tumor selective cytotoxicity.

This object is met by the present invention according to which an antitumor effect is generated by a combination of an oxidoreductase, which is chemically conjugated with biocompatible polymer, and a substrate for the oxidoreductase.

The antitumor agent according to the present invention is a combination of an active enzyme component (A) and of its substrate (B). The active enzyme component (A) is an oxidoreductase, which is chemically conjugated with a polymer. Upon administration of (A) and later on administration of (B), an active molecular species(C), such as a peroxide, is formed.

The active enzyme component(A), by its polymer conjugation, possesses a tumor targeting property. Namely, the antitumor agent exhibits a selective accumulation in tumor tissue and exerts an antitumor action if a known substrate (B) for the active enzyme component (A) is injected thereafter. Due to the enzyme reaction, an active free radical components (C) ($O_2^{*-}$ and $H_2O_2$ are formed. Both xanthine oxidase conjugated with poly(ethylene glycol) (A) and substrate (B) show no toxicity by themselves. The potent antitumor activity is only apparent when its substrate (B) is separately administered later. By doing so, less systemic toxicity is seen while exhibiting a remarkable antitumor activity. Thus the present invention offers great benefit.

SUMMARY OF THE INVENTION

Figure 1:
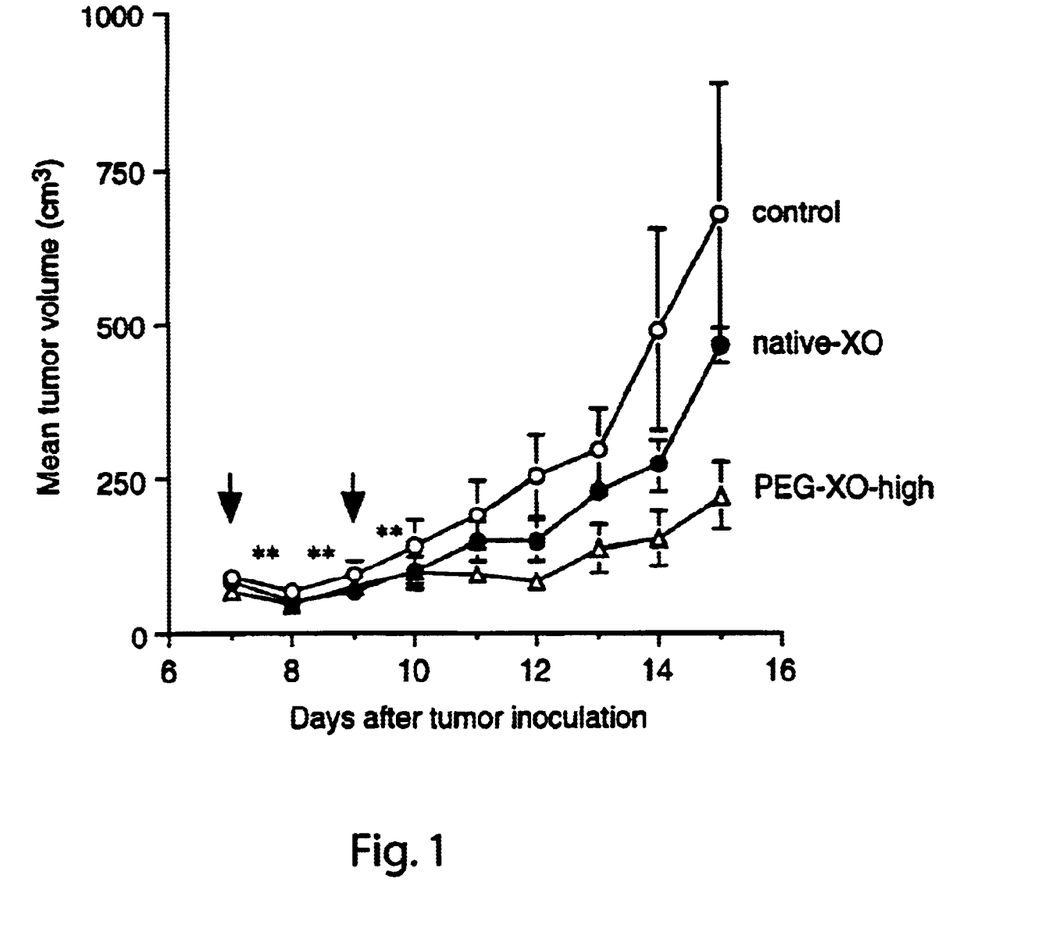
FIG. 1 shows the effect of native-XO and PEG-XO-high on the growth of S-180 solid tumor in ddY mice (2 times administration)

The present inventors have found a significant enhancement of tumor accumulation of XO in tumor tissue after the XO has been chemically conjugated with a polymer, like poly(ethylene glycol) (hereinafter called "PEG"; chemically conjugated XO with PEG is hereinafter called "PEG-XO"), and hence the remarkable antitumor effect of such conjugates, like PEG-XO. Conjugation of PEG to the ε-amino group of lysine residues on the molecular surface of XO would reduce the binding affinity to endothelial cells which contain a high level of anionic charges. The masking of cationic amino groups with PEG reduces the binding of PEG-XO to endothelial cells resulting in an enhanced blood circulation time and hence in an accumulation of PEG-XO in the tumor by the EPR effect. By administrating hypoxanthine, the substrate of XO, subsequent to the administration of PEG-XO, a tumor selective antitumor action can be accomplished by the product of this enzyme reaction, which is the peroxide (FIG. 1).

As mentioned below, the above effects can be accomplished also by using other oxidoreductases besides XO with the subsequent administration of their appropriate substrates. The oxidoreductases can be chemically conjugated with various polymers other than PEG.

When using the invention in practice, a therapeutically effective amount of the oxidoreductase chemically conjugated with a polymer is administered to a patient. Subsequently, a substrate of the oxidoreductase is administered.

DESCRIPTION OF THE PREFERRED EMBODIMENT

As the oxidoreductases used in the present invention, there may be cited, for example, xanthine oxidase, D-amino acid oxidase, glucose oxidase, galactose oxidase, etc., among which xanthine oxidase is preferably used.

If xanthine oxidase is used as an oxidoreductase, its substrate is hypoxanthine or xanthine. Substrates of D-amino acid oxidase, glucose oxidase and galactose oxidase are D-amino acids, glucose and galactose, respectively.

These oxidoreductases are chemically conjugated with polymers. Although a preferred polymer moiety for conjugation in the present invention is PEG, both naturally occurring and synthetic polymers which show little antigenicity or immunoreactivity may be utilized, i.e., polysaccharides such as pullulan, chitosan, hyaluronic acid, heparin, heparin sulfate or their derivatives, etc., gelatin/collagen and their derivatives, copolymers of D-glutamic acid and L- or D-lysine, and/or other amino acids such as D/L-alanine and poly(aspartic acid) derivatives, their copolymers and other polypeptide-containing appropriate amino acids, copolymers of styrene and maleic acid, poly(lactic acid), hydroxypropyl- or isopropyl-methacrylamide copolymer (HPMA copolymer), poly(vinyl alcohol) (PVA), poly (vinylpyrrolidone), pyran copolymers, etc., and combinations thereof.

The chemical conjugation of oxidoreductases with any modifier can be carried out by conventional methods previously described which use various compounds having functional groups such as cyanurylchloride, carbodiimides, acidanhydrides, aldehydes, acylchlorides, succininide isothiocyanates, etc. The reaction is directed to amino, carboxyl, thiol, etc and will be carried out under relatively mild conditions, low temperature, neutral to slightly alkaline pH in an aqueous solution to avoid denaturation of the enzyme. It may be carried out also in solvents including liquid ammonia. Furthermore, a modification of amino acid residue(s) involving enzyme activity should be avoided. As a preferred example, conjugation of XO with PEG is described below.

XO is an oxidoreductase which uses hypoxanthine or xanthine as a substrate and produces uric acid and various reactive oxygen molecular species including peroxide ($O_2^{*-}$) and $H_2O_2$ though to a small extent. XO can be easily obtained from bovine milk, however the source of XO is not limited to the bovine milk in the present invention.

According to the previous findings by the present inventors, PEG is one of the suitable polymers to be used for conjugation. It is well known that PEG is biocompatible and reduces immunogenicity of foreign proteins upon conjugation and further enhances the blood circulation time of the conjugates (cf: in Poly(ethylene glycol) Chemistry: Biotechnical and Biomedical Applications, by Harris, J. M. Ed., Plenum: New York, 1992, p.153–169). Activated PEG can be obtained by several methods such as a condensation reaction between carboxylated PEG and N-hydroxysuccinimide.

Other than ordinary single chain PEG, biantennary PEG, which has double branched PEG chains at a single conjugation point can be also used. This biantennary PEG is synthesized using succinimidyl branched PEG. It has several advantages as a modifier of oxidoreductase, such as more reduction of immunogenicity and increased stability against temperature or various proteases.

Conjugation of XO with PEG is carried out in 50 mM sodium phosphate buffer pH 7.4, at room temperature or lower, for 30 to 60 min in this case. The extent of conjugation can be controlled by changing the feed ratio of activated PEG to lysyl residues in XO. In the present example, XO conjugated to 17–50% of lysine residues with succinimidyl PEG was obtained by adding a 1.2–6.7 molar excess of PEG to 1 mole of lysine in XO.

PEG-XO or other biocompatible macromolecules can be selectively delivered to a solid tumor due to the EPR effect as described earlier (or see Cancer Res., vol. 46, p.6387–6392, 1986). By administration of hypoxanthine or xanthine by injecting it intravenously after the adequate accumulation of PEG-XO in the tumor, but after clearance in the general circulation or in normal organs, XO at the tumor site generates reactive oxygen molecular species such as $O_2^{*-}$ and $H_2O_2$, and exerts a unique antitumor action without systemic side effects.

Figure 2:
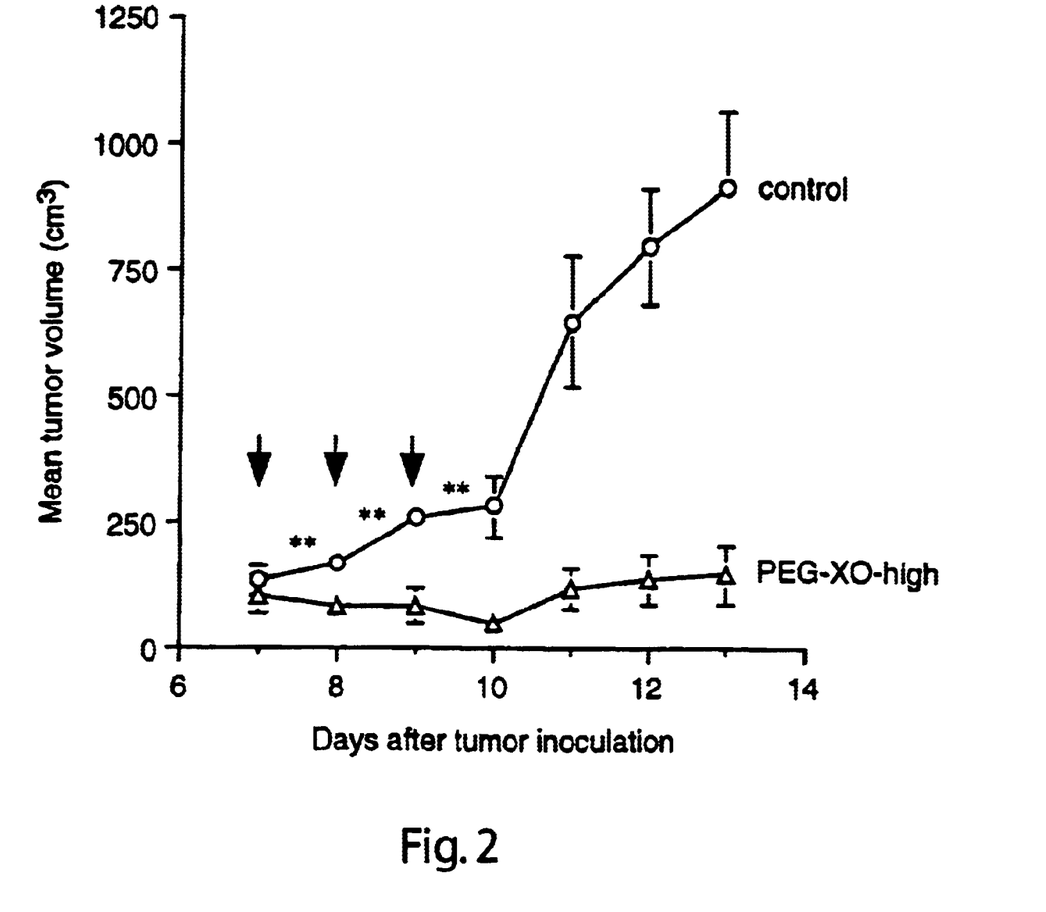
FIG. 2 shows the effect of PEG-XO-high on the growth of S-180 solid tumor in ddY mice (3 times administration).

The results of this therapeutic strategy using XO and hypoxanthine against S-180 solid tumor model in mice demonstrates the significant suppression of tumor growth (FIGS. 1 and 2). These results suggest that: i) reactive oxygen molecular species, which are generated by the reaction between XO and hypoxanthine, have a potent antitumor activity, and ii) the reaction between XO and hypoxanthine occurs in the solid tumor or around its periphery. In contrast thereto, native XO showed no significant antitumor activity under the conditions used (FIG. 1).

Figure 3:
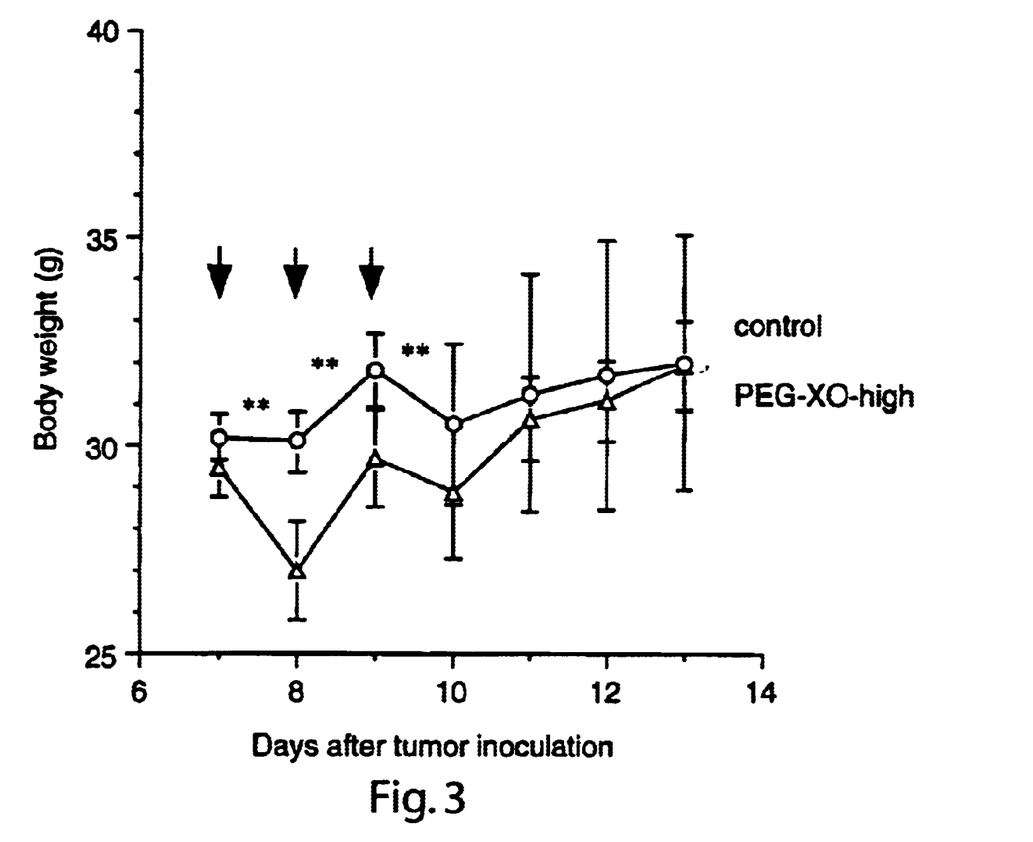
FIG. 3 shows the body weight change of ddY mice with and without a treatment with PEG-XO-high/hypoxanthine.

Systemic side effects of PEG-XO/hypoxanthine therapy, which were evaluated using body weight as a parameter, seem to be not so significant. The results showed only a transitory body weight loss, on day 8–9, but recovered recovery on day 10 (FIG. 3). No serious or significant hematotoxicity or liver toxicity was seen.

For treating cancer by using the antitumor agents of the present invention, a therapeutically effective amount of a chemically conjugated oxidoreductase is first administrated, and after allowing a lapse of adequate time for the accumulation of the chemically conjugated oxidoreductase in the tumor, its substrate is administrated. The effective and low-toxicity dosage of the substrate is 10–100 mg/kg body weight/day.

The proper time to administer it the substrate is preferably 6 to 100 hs after the administration of the chemically conjugated oxidoreductase.

The antitumor agents of the present invention may be administered in the form of an injection or an oral dosage. In the case of injection, any subcutaneous, intramuscular, intravenous, intraarterial or local/direct injection is applicable. The type of preparation for oral administration may be selected. Some examples are tablets, granules, pills, liquid medicines, either an oil or aqueous syrup, troches, and drops.

EXAMPLES

The present invention is described by examples shown below in detail which do not limit the scope of the invention.

Synthetic Procedures

Example 1

Synthesis of PEG-XO

XO from bovine milk (Sigma Chemicals, St. Louis, Mo., USA) was first purified by ultrafiltration and concentrated with the use of an Amicon system with a PM 30 membrane (cutoff size 30,000). The concentration of the XO solution was adjusted to 10 mg/ml protein with 50 mM sodium phosphate buffer (pH 7.4). To the XO solution, succinimide activated-PEG (Mw 5000, Shearwater Polymers, Huntsville, Ala.) was added at molar ratios of PEG over the ε-amino group of lysine in XO, of 1.2 and 6.7, respectively, to prepare PEG-XOs having a low and a high extent of PEG conjugation.

Unreacted PEG derivatives with functional groups, decomposed components, and other impurities were removed similarly by ultrafiltration using a PM-10 membrane as mentioned above. The conjugates thus obtained were stored in 50 mM sodium phosphate buffer (pH 7.4) containing 1 mM sodium salicylate at 4° C.

Physicochemical and Biochemical Characteristics

Example 2

Determination of the Extent of the PEG Conjugation

The extent of the PEG conjugation was determined by the loss of free amino groups as a result of the PEG-coupling. 2,4,6-Trinitrobenzenesulfonic acid was used to quantify the free amino groups of PEG-XO spectroscopically as described by Fields (Methods Enzymol., vol.25, p.464–468, 1972). Glycine was used as a standard amino acid. The protein concentrations of both native XO and PEG-XO were quantified by using the DC Protein Assay kit (Bio-Rad Laboratories, Hercules, Calif., USA). The excess feed molar ratio of succinimidyl PEG at 1.2 or 6.7 to ε-amino groups of lysine in XO resulted in 17% or 49% conjugation of PEG to XO, respectively. PEG-XO having a portion of PEG of 17% or 49% modified amino groups by the conjugation are hereinafter referred to as "PEG-XO-low" and "PEG-XO-high", respectively.

The molecular weights of these PEG-XO conjugates were 383 kDa or 543 kDa, respectively, which were estimated on the basis of the conjugation degree, ie., of the loss of amino groups as obtained by the TNBS assay. The results are shown in the Table 1.

TABLE 1

Physicochemical and Biochemical Characteristics of Native-XO and PEG-XO

|  | Feed ratio (PEG/amino group molar ratio) | % conjugated | Mw (kDa) | XO activity (U/mg protein) |
|---|---|---|---|---|
| Native-XO | — | 0 | 298 | 2.12 |
| PEG-XO-low | 1.2 | 17 | 383 | 2.40 |
| PEG-XO-high | 6.7 | 49 | 543 | 1.15 |

Example 3

Size Exclusion Chromatography

Figure 4:
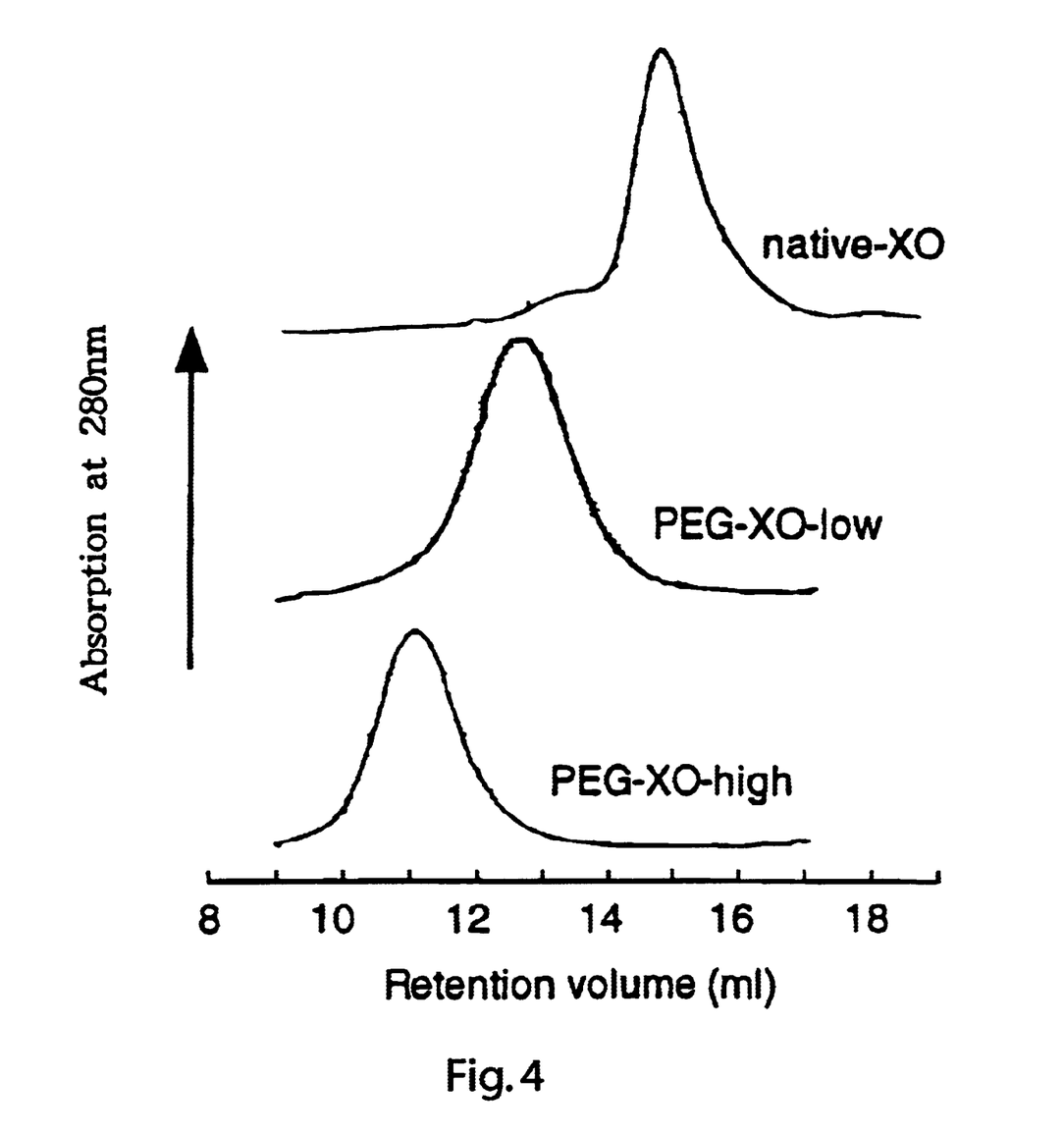
FIG. 4 shows a size exclusion chromatocraphy of native-XO and PEG-XO.

The increase of the molecular size of XO after PEG conjugation was demonstrated by means of size exclusion chromatography using the FPLC system (Pharmacia LKB, Uppsala, Sweden) equipped with a Superose 6 HR 10/30 column (Pharmacia LKB) using a mobile phase of 50 mM sodium phosphate buffer (pH 7.4). Elution of the conjugates were detected at 280 nm (FIG. 4).

Example 4

Enzyme Activity of PEG-XO

The enzyme activity was determined by quantifying the formation of uric acid from hypoxanthine by measuring the increase of absorbance at 290 nm, an absorption maximum of uric acid. The initial concentration of the substrate hypoxanthine was 50 μM. The enzyme reaction was carried out in 50 mM sodium phosphate buffer (pH 7.4) at room temperature. One unit of XO activity is defined as the velocity of the formation of 1 μmol of uric acid per min. The results are shown in Table 1.

PEG-XO-low showed slight increase of the activity (110%) compared with native XO. PEG-XO-high, even after a 49% conjugation of the amino group, retained 54% of the original enzyme activity of native XO.

Pharmacokinetic Studies

Example 5

In vivo Distribution of PEG-XO Conjugate After Intravenous Injection

In vivo distribution of native XO and PEG-XO-high was examined using radioemitting $^{125}$I-labeled derivatives. Both radiolabeled native-XO and PEG-XO-high were prepared by the chloramine T method.

Sarcoma 180 tumor cells were implanted subcutaneously with 2×10$^6$ cells in male ddY, 6-week-old mice, weighting 30–35 g, from SLC Inc., Shizuoka, Japan. The organ or tissue distribution study was performed on day 7–10 after the tumor inoculation, when the tumors were 5–7 mm in diameter, but contained no necrotic region.

$^{125}$I-Labeled native-XO or PEG-XO-high was administered to mice via the tail vein (100 μl/mouse). After 24 h, the mice were sacrificed, and blood samples were drawn by cardiac puncture, and they were then subjected to reperfusion with heparin containing saline to remove blood components in the blood vessels of the tissues. The tumor tissue as well as normal tissues including the brain, liver, spleen, muscle, skin, heart, lung, colon, and kidney were collected and weighed. The radioactivities of those tissues were measured by a gamma counter.

Figure 5:
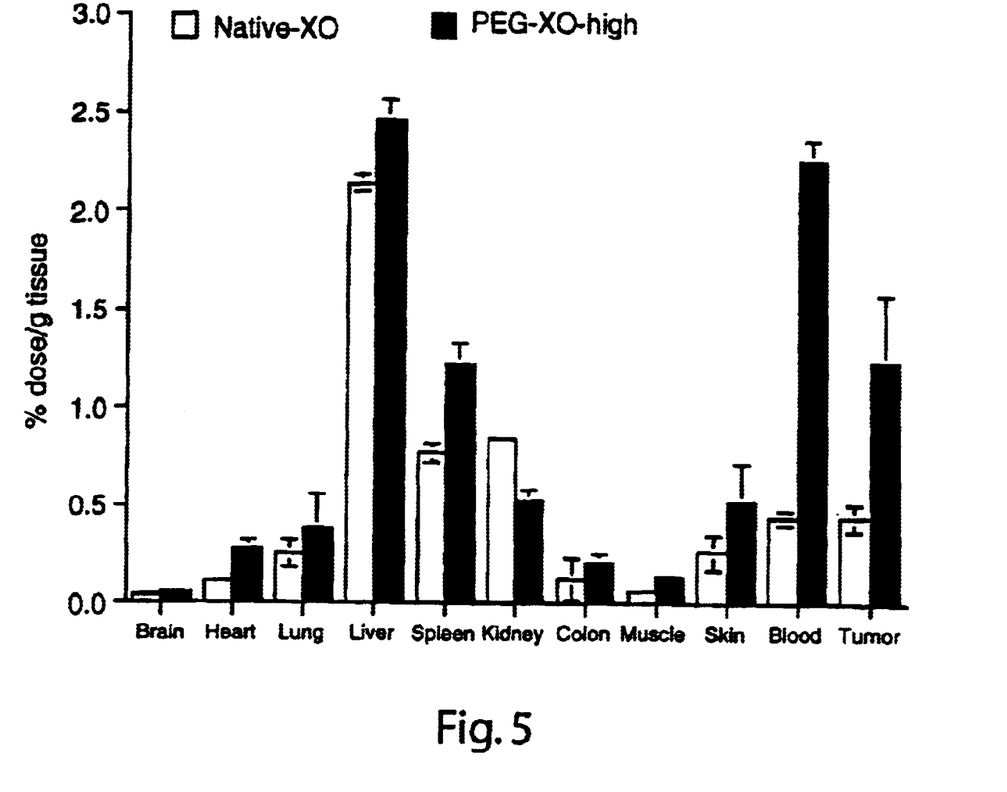
FIG. 5 shows the body distribution of $^{125}$I-labelled native-XO and PEG-XO-high after intravenous injection to ddY mice bearing S-180 solid tumor.

As shown in FIG. 5, PEG-XO-high was found to significantly improve both the blood and the tumor accumulation compared with that of native-XO, whereas slight or negligible increase in accumulation in other normal organs was observed for PEG-XO-high. Furthermore, less accumulation of PEG-XO-high in the kidney was observed than with native-XO.

Example 6

Time Course of Tumor Accumulation of PEG-XO Conjugate

The time course of the tumor accumulation of PEG-XO-high was examined by measuring the enzyme activity derived from PEG-XO-high in the tumor tissue. Tumor bearing mice were prepared as described above. PEG-XO-high (2U/ml, 100 µl) was injected intravenously (i. v.) to the mice. After a given period, the tumor tissue was removed as described above. The tumor tissue was then homogenized with three volumes of 20 mM potassium phosphate buffer pH 7.6 which contained 2 mM ethylenediaminetetraacetic acid, 2 mM amidinophenylmethanesulfonyl fluoride, 10 mM dithiothreitol, 0.5 µg/ml of leupeptin. The homogenates were centrifuged at 10,000 g for 20 min, and each supernatant was applied to a FPLC system with a Superose 6 HR 10/30 column similar to the previous section. The enzyme activity of the PEG-XO-high fraction was determined fluorometrically, i. e. , the formation of fluorescent isoxanthopterin from pterin was measured with an excitation at 345 nm and an emission at 390 nm, in which hypoxanthine was replaced with pterin as substrate. The quantification was made using the calibration curve of the authentic isoxanthopterin (Aldrich Chemical, Milwaukee, Wis.).

Figure 6A:
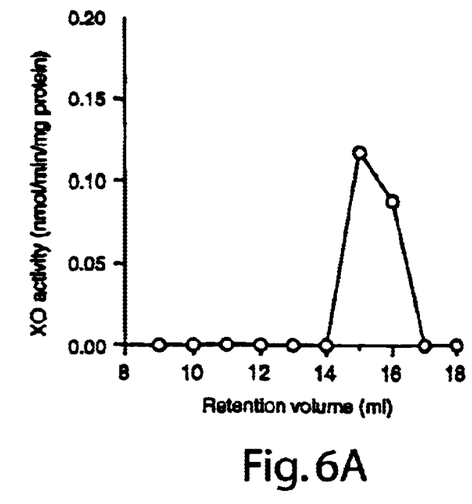
FIGS. 6A and 6B shows the XO activity of S-180 solid tumor tissue before and 24 hrs after a PEG-XO high injection, respectively

The tumor accumulation of PEG-XO-high with its enzyme activity was demonstrated by measuring the XO activity of the homogenate of the tumor before and 24 hrs after the PEG-XO high injection. The results are shown in FIG. 6. In S-180 solid tumor tissue without the administration of PEG-XO-high, XO activity appears only in a fraction corresponding to native XO. This means that small amount of XO had existed in the tumor tissue endogenously (FIG. 6A). On the other hand, with the solid tumor tissue after PEG-XO-high injection (0.2 U/mouse), a new large peak of XO activity was observed at the molecular weight range different from native XO. This new peak consisting of fraction numbers of 11, 12, and 13 corresponds to the molecular weight range of PEG-XO-high as demonstrated in FIG. 4.

Figure 6B:
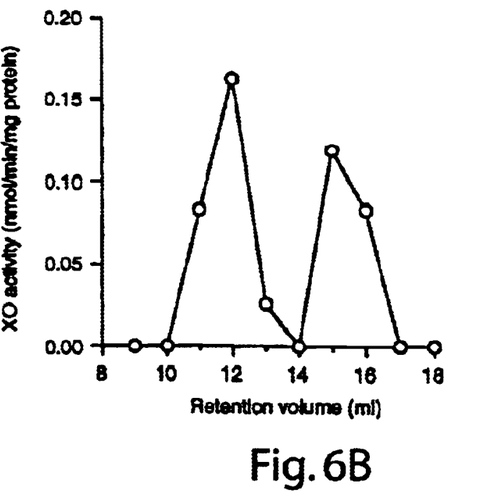

Thus, FIGS. 6A and 6B show that the XO activity in tumor, corresponding to the molecular weight range of PEG-XO-high, appeared after the PEG-XO-high administration.

Figure 7:
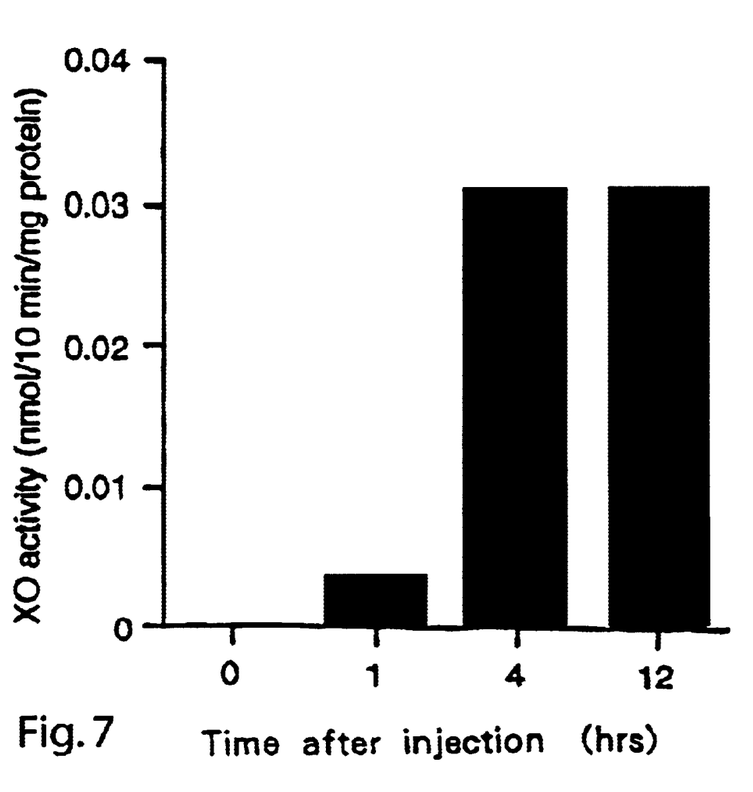
FIG. 7 shows time dependent accumulation of PEG-XO-high in tumor tissue.

In addition, the PEG-XO-high activity increased in a time dependent manner (FIG. 7).

Antitumor Activity in vivo

Example 7

Antitumor Activity of PEG-XO in vivo

Sarcoma 180 cells were implanted subcutaneously with $2 \times 10^6$ cells in male ddY, 6-week-old mice, weighting 30–35 g. When the tumors became palpable (5–7 mm in diameter), usually 7 days after implantation the treatment was resumed.

After native-XO or PEG-XO-high was intraveneously injected (2 times, 0.6 U/mouse, the first time 7 days and the second time 9 days after the tumor inoculation) to the mice. Hypoxanthine (13.3 mg/kg) was injected intraperitoneally six times, each time more than 6 hrs after the last time, as indicated by asterisks (*) in the FIGS. 1 to 3. A significant ($p<0.05$) suppression of the tumor growth was observed in mice administered with PEG-XO-high. However, a similar treatment by native XO showed no significant reduction of the tumor growth (FIG. 1). The weights of tumor 15 days after the tumor inoculation were 0.36±0.12 g (control), 0.31±0.03 g (native XO treatment), and 0.22±0.05 g (PEG-XO-high treatment), respectively, which indicates that 39% inhibition of the tumor growth was achieved by only twice administration of PEG-XO-high.

By three administrations of PEG-XO-high (on 7, 8, and 9 days after the tumor inoculation, 0.6 U/mouse) and subsequent 6 intraperitoneal injections of hypoxanthine (13.3 mg/kg) as indicated by asterisks (*), a remarkable antitumor activity of PEG-XO-high was observed (FIG. 2) 13 days after the tumor inoculation, the weights of the tumor were 0.57±0.24 g (control) and 0.13±0.08 g (PEG-XO-high treatment), corresponding to a 77% inhibition of tumor growth by PEG-XO-high.

Example 8

Systemic Side Effect of PEG-XO

In order to examine the systemic side effect of PEG-XO-high administration, the change of the body weight after the PEG-XO-high administration was investigated. PEG-XO-high was intravenously injected 3 times (on 7, 8, and 9 days after the tumor inoculation, 0.6 U/mouse). Hypoxanthine (13.3 mg/kg) was intraperitonealy injected 6 times as indicated by the asterisks (*).

As shown in FIG. 3, a slight but significant decrease of the body weight was observed on day 8 and day 9, but then the body weight recovered to normal level on about day 10 or later. Thus, toxicity is reversible and transitory.

What is claimed is:

1. A method of treating malignant tumors comprising the steps of sequentially administering a first component A, xanthine oxidase, which is chemically conjugated with a polyethylene glycol, and six to one hundred hours thereafter, separately administering component B, a substrate selected from the group consisting of hypoxanthine and xanthine, each of which is a substrate for the xanthine oxidase.

* * * * *